(12) United States Patent
Nahum et al.

(10) Patent No.: US 9,237,861 B2
(45) Date of Patent: Jan. 19, 2016

(54) METHOD FOR THE AUTOMATED AND ASSISTED ACQUISITION OF ANATOMICAL SURFACES

(75) Inventors: Bertin Nahum, Baillargues (FR);
Fernand Badano, Villeurbanne (FR);
Pierre Maillet, Saint Aunes (FR);
Alexander Habermeier, Montpellier (FR); Patrick Dehour, Crespian (FR)

(73) Assignee: MEDTECH, Castelnau le Lez (FR)

( * ) Notice: Subject to any disclaimer, the term of this patent is extended or adjusted under 35 U.S.C. 154(b) by 413 days.

(21) Appl. No.: 13/810,186

(22) PCT Filed: Jul. 20, 2011

(86) PCT No.: PCT/FR2011/051747
§ 371 (c)(1),
(2), (4) Date: Jan. 14, 2013

(87) PCT Pub. No.: WO2012/017167
PCT Pub. Date: Feb. 9, 2012

(65) Prior Publication Data
US 2013/0113798 A1    May 9, 2013

(30) Foreign Application Priority Data

Aug. 4, 2010 (FR) ...................................... 10 56428

(51) Int. Cl.
*A61B 5/107* (2006.01)
*A61B 19/00* (2006.01)
*G06F 19/00* (2011.01)
*G06K 9/00* (2006.01)
*A61B 5/117* (2006.01)

(52) U.S. Cl.
CPC ........... *A61B 5/1077* (2013.01); *A61B 19/5212* (2013.01); *G06F 19/321* (2013.01); *G06F19/3481* (2013.01); *G06K 9/00281* (2013.01); *A61B 5/1176* (2013.01); *A61B 19/5244* (2013.01); *A61B 2019/5231* (2013.01); *A61B 2019/5265* (2013.01)

(58) Field of Classification Search
CPC ..................... G06T 2019/5289; G06T 7/0057; G06T 17/00; G06T 2207/10028; G06T 2207/10072; G06T 2207/30004; G06T 2207/30016; G06T 7/0024; G06T 7/0028; G06T 2207/10081; G06T 2207/10088; G06T 2207/30068; G06T 2207/30196; G06T 3/0068; G06T 7/0046; G06T 2207/10136; G06T 2207/20101; G06T 2207/1032; G06T 2207/20092; G06T 11/00; A61B 2019/5291; A61B 5/065; A61B 6/5247; A61B 8/5238; A61B 19/56; A61B 2019/5272; A61B 2019/5276; A61B 2019/5287; A61B 5/055; A61B 19/50; A61B 6/032; A61B 8/483; A61B 8/13; A61B 8/469; G06F 19/3437; G06F 19/321; G06K 2209/05; G06K 9/00033; G06K 2009/366; G06K 2209/051; Y10S 128/916
See application file for complete search history.

(56) References Cited

U.S. PATENT DOCUMENTS

2008/0037714 A1 * 2/2008 Sakaida et al. ................ 378/207

FOREIGN PATENT DOCUMENTS

FR    2871363 A1    12/2005
FR    2917598 A1    12/2008

*Primary Examiner* — Haixia Du
(74) *Attorney, Agent, or Firm* — Andrew W. Chu; Craft Chu PLLC

(57) ABSTRACT

The method for the automated and assisted acquisition of anatomical surfaces includes a first acquisition of the surfaces undertaken in order to create a first numerical model and a perioperative second acquisition undertaken by scanning the surfaces in order to create a second numerical model for identifying the coordinates of the surfaces. The surfaces are supported by a robotic arm; and then the models are brought into correspondence by resetting. The scanning in the second acquisition includes making a preliminary identification of the coordinates of noteworthy points on the surfaces manually, assisted by the robotic arm, and the identifying parts a the points, in order to construct a reference frame and to determine a scanning region; creating an intermediate model from the reference frame and at least one of the points; preliminary resetting the first model with the second model; and automatically scanning the determined zone.

12 Claims, 1 Drawing Sheet

METHOD FOR THE AUTOMATED AND ASSISTED ACQUISITION OF ANATOMICAL SURFACES

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention is related to the medical field, in particular in operative methodology during the preparation and carrying out of surgical interventions.

The invention relates in particular to medical imaging and, in the perioperative phase, to the automated acquisition of anatomical surfaces, in particular of a patient's head and face, then the surface resetting of the acquired images with respect to images stored in pre-operative phase.

The invention will find an application in the assistance by robotics for the acquisition of anatomical surfaces and for the surface resetting.

To this end, the present invention relates to a method for automated and assisted acquisition of anatomical surfaces.

2. Description of Related Art Including Information Disclosed Under 37 CFR 1.97 and 37 CFR 1.98

In a known way, during a surgical operation on a patient, in particular within the framework of the neurosurgery at the level of a patient's head, the doctor uses systems providing an assistance, in particular by improving the surgical accuracy. To this end, such systems permit, in the perioperative phase, the acquisition of the anatomical surfaces aimed by the operation, then their resetting with respect to images already recorded, for example previously, during a pre-operative phase during an X-ray examination (CT-scan) or an MRI (stands for Magnetic Resonance Imaging). It is thus possible for the doctor to accurately localize the patient with respect to the imaging for the operation.

In particular, the acquisition consists in identifying the actual position of the patient's anatomical zone, by performing a scanning of the surface of said zone using a pointer, for example in the form of a mechanical point, ultrasonic waves or a laser beam. The system then performs a surface resetting in the form of a comparison between this identification and the images recorded previously in the pre-operative phase, calculating the bringing into correspondence of the existing images with the patient's body at the time of the operation. In brief, for each identified point, an evaluation is performed so as to cause the acquired scatter diagram to correspond to the pre-recorded images.

Therefore, the way of performing the step of acquisition of the anatomical surfaces has a considerable influence on the accuracy of the operation that will follow. Several acquisition systems exist nowadays, which use different techniques for identifying the anatomical surfaces.

A first solution consists in positioning, at different particular places of the zone to be acquired, markers, in the form of a mask or pads, directly glued on the skin. These markers are then identified in the space by scanning with a mechanical point or a transmission/receiving beam, namely a laser.

The main drawback of such a scanning resides in its lack of accuracy, which depends on the way of localizing said markers as well as their number and their spatial distribution on the skin. The resetting resulting from the same is then little reliable, i.e. it exhibits important variations and shifts at the level of the surfaces located between the markers.

In addition, the markers can move, because of the elasticity of the skin, even detach. The placing of the markers also obliges to shave the portion of the cranium.

An alternative solution consists in passing over the anatomical zone with a pointer, the coordinates of which are located in the space, in particular through cameras.

According to an embodiment, said pointer can be mechanical, being in the form of a probe, the point of which enters directly into contact with the skin. Said point is manually displaced from one point to another, namely on the morphologically noteworthy points, and along particular anatomical lines of the zone involved, while its different positions and contact points are recorded in three dimensions.

However, though this technique permits to identify a larger number of points of the surface, it remains limited as to the number of points identified, about one hundred, requiring a restriction of the identification to determined lines and determined noteworthy places of the patient's anatomy. This restriction, due to the intervention by the operator, has automatically an influence on the quality of the subsequent surface resetting. Furthermore, the deformation of the skin during the scanning with the pointer is another cause for inaccuracy.

An alternative resides in a contactless pointer, permitting to obtain a larger number of points identified in a smaller period of time. Such a pointer is in the form of a light-radiation transmitter, such as a laser beam. Said transmitter is held in hand by the practitioner, who scans the anatomical zone with the laser.

A first known device comprises a transmitter in the form of a laser telemeter, the position and the orientation of which are constantly identified in the space, permitting to obtain the coordinates of each point recorded by the telemeter.

However, the accuracy of the identification by the telemeter remains limited. That is why it has been devised to directly record the impact of the emitted laser beam at the level of the skin. To this end, the transmitter transmits, on the one hand, a laser beam in the visible light spectrum, in order to allow the practitioner to display the point of impact and its scanning of the patient's anatomical zone and, on the other hand, a beam of invisible light, such as the infrareds, which are captured by specific sensors. Specifically, the reflection of the infrareds at the point of impact permits to accurately identify the position of said point in the space.

It should be noted that the localization of the telemeter or the point of impact of the laser beam uses an optical triangulation principle using various cameras.

Despite these various evolutions, the existing identification and scanning systems are not completely satisfactory.

Indeed, the scanning always occurs manually, creating a human factor, which reduces the accuracy of the identification, but also its repeatable nature, i.e. the scanning paths remain approximate and completely related to the practitioner.

In order to cope with these drawbacks, it has been devised to couple the transmitter to a robot. Such solutions are described in WO 2009/013406, WO 2005/122916 and WO 2005/032390.

In particular, the transmitter is fixed to the end of a robotized arm, hinged so as to have degrees of freedom of movement in the three dimensions. The position of the transmitter and the data it records are then identified in the space with respect to the reference system of said robotized arm.

In particular, a first previous acquisition of said anatomical surfaces is performed, so as to create a three-dimensional representation in the form of a first digital model; then, a second perioperative acquisition by scanning said surfaces is performed, so as to create a three-dimensional representation in the form of a second digital model; then, said scanning is performed with means for identifying the coordinates of said surfaces, said means being supported by a robotized arm; and finally a bringing into correspondence by resetting said first and second models is performed.

Therefore, one observes that the resetting of the models is not optimal, requiring the intervention of a data-processing operator, in order to try to cause the models to match. When this fails, it is necessary to repeat the scanning operation, increasing that more the duration of the intervention.

In addition, even though such devices permit to avoid depending from the operator, by automating the scanning of the anatomical surface, with a highly reproducible nature, this automation considerably limits the capabilities of adaptation of these devices with respect to the anatomical zone, in particular with respect to the different morphologies of the patients.

Furthermore, in all cases the existing devices use means for navigating within the display of the three-dimensional digital model obtained from the images so acquired. These navigation means necessarily require the identification of the transmitter, as previously evoked, thereafter of the surgical instruments.

SUMMARY OF THE INVENTION

The aim of the invention is to cope with the drawbacks of the state of the art by providing a method for automated and assisted acquisition of anatomical surfaces, which combines the accuracy of a scanning assisted by a robotized arm with the adaptability of a manual scanning, while permitting the acquisition of a large number of points.

In particular, the invention foresees to perform a preliminary scanning manually controlled by the practitioner, with a transmitter supported by said robotized arm, permitting, on the one hand, to determine a specific zone for a subsequent fully automated scanning and, on the other hand, to perform a first surface resetting increasing the accuracy of the final surface resetting.

To this end, in such a method:
  a first previous acquisition of said anatomical surfaces is performed, so as to create a three-dimensional representation in the form of a first digital model;
  a second perioperative acquisition by scanning said surfaces is performed, so as to create a three-dimensional representation in the form of a second digital model;
  said scanning being performed with means for identifying the coordinates of said surfaces, said means being supported by a robotized arm;
    then
  a bringing into correspondence by resetting said first and second models is performed.
  Said method is characterized in that the scanning consists of:
    performing a preliminary identification of the coordinates of the noteworthy points of said anatomical surfaces by manual displacement, assisted by said robotized arm, of said means for identifying at the level of said noteworthy points, so as to construct a reference frame and to determine a scanning zone for said anatomical surfaces;
    creating an intermediate model from said reference frame and at least one of said noteworthy points;
    performing a preliminary resetting of said first model with said second model;
    performing an automatic scanning of the determined zone.

Thus, the method according to the invention provides an increased accuracy in the scanning being performed and the identification of a larger quantity of anatomical points of the zone involved, with an automated and reproducible accuracy of the path, while adding a manual and adaptable nature through the initial manipulation by an operator.

Another advantage of the present invention resides in the use of a robotized arm, which then serves as a reference frame. The anatomical zone to be scanned, then the model extracted from this acquisition are localized with respect to this reference frame, so that thereafter, after resetting, the same reference frame of the robotized arm serves for positioning the surgical instruments for the operation.

According to other features, said method consists of:
  performing an identification of the coordinates of at least three noteworthy points;
  determining a fourth point from one of said three noteworthy points by symmetry according to an axis passing through the other two of said noteworthy points; and
  determining a reference frame for calculating the path of the automatic scanning, said reference frame being formed of at least two axes, each comprising a pair of said four noteworthy points.

Advantageously, said method consists of performing an identification of the coordinates of at least one central point, said central point being located at the intersection of said axes.

According to one embodiment, the method consists in recording said central point at the level of the first model; and in that said preliminary resetting is performed by bringing into correspondence the central point with at least another noteworthy point.

According to another embodiment, it consists in performing the bringing into correspondence of said first model with said intermediate model by matching said axes.

According to the preferred application, said anatomical surfaces correspond to the face and said axes follow at least partially the nose rim and a frontal line.

According to another facultative feature, the method consists in determining a reference frame centered on said robotized arm.

Further features and advantages of the invention will become clear from the following detailed description of the non-restrictive embodiments of the invention, with reference to the attached figures.

DETAILED DESCRIPTION OF THE DRAWINGS

Figure 1:
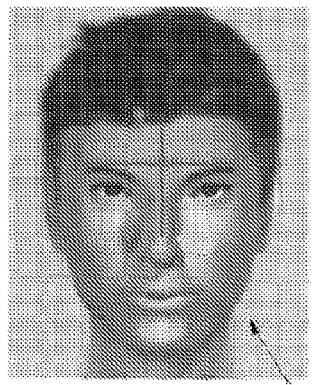
FIGS. 1, 2 and 3 represent a schematic front view of three steps of the method according to the invention applied to a patient's face.

The present invention relates to a method for automated and assisted acquisition of anatomical surfaces.

Specifically, such a method combines a manual intervention with a robotic assistance, then a fully automatic robotized operation.

It should be noted that the anatomical surfaces in the meaning of the invention can comprise any portion of a patient's body. According to the example shown in the figures, according to the preferred embodiment, said anatomical surfaces correspond to the face 1 of said patient.

In a first step, prior to the operation, a first previous acquisition of said anatomical surfaces of the patient is performed. Such a previous acquisition can be obtained by any kind of means, in particular through a scanner or an IRM.

From this previous acquisition, a three-dimensional representation in the form of a first digital model 2 is created.

Then, in the perioperative phase, a second acquisition is performed by scanning of said anatomical surfaces. From this second acquisition, a three-dimensional representation in the form of a second digital model 3 is created.

Finally, a bringing into correspondence by surface resetting of said thus obtained first 2 and second 3 models is performed. In brief, a superposition of said models 2 and 3 is performed in order to cause both representations to coincide, the second model 3 covering said first model 2.

Figure 5:
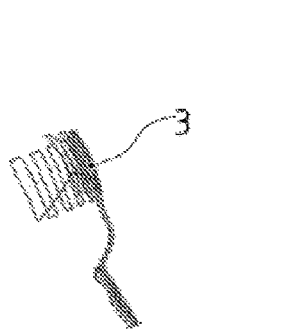
FIGS. 5, 6 and 7 schematically represent three views of the surface resetting of the method according to the invention.
Figure 6:
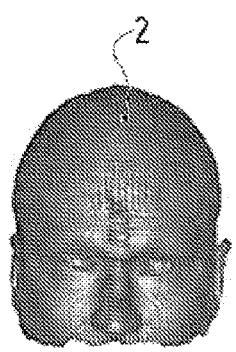
Figure 7:
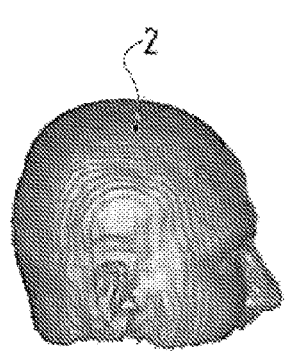

This resetting step is represented in FIGS. 5 to 7, FIG. 5 representing the second model 3, while FIGS. 6 and 7 represent the superposition of said second model 3 on the first model 2, according to a profile view and a front view of the anatomic surface involved, i.e. a patient's head, respectively.

In particular, said resetting can be based on an algorithm for resetting three-dimensional data, referred to as ICP (stands for <<iterative closest point>>). Generally, the ICP algorithm consists in iteratively calculating the rigid transformation matrix (rotation and translation) resetting in the best way two sets of data defined by their coordinates in a three-dimensional identification.

Advantageously, an essential feature of the present invention resides in that said scanning is performed by means for identifying the coordinates of said anatomical surfaces.

In particular, these identification means cam measure in the space and determine the coordinates of points of said surfaces with respect to a reference system.

Preferably, said identification means are supported by a robotized arm. The latter is designed movable and controlled so as to provide it with degrees of freedom of movement according to the three dimensions. Therefore, said reference system, with respect to which the coordinates of the points of said anatomic surface are measured, is determined by said robotized arm.

It should then be noted that the patient is immobilized with respect to the base on which said robotized arm rests and moves.

In this respect, said robotized arm serves as a reference frame, during the acquisition, but also for the subsequent further operations.

In particular, the data-processing means and the calculator associated with said robotized arm permit to centralize the spatial identification of the patient's body, but also of the tools necessary for the acquisition and the scanning of the anatomical surfaces, as the transmitter positioned at the end of said arm, but also for the surgical tools that will intervene in the operative phase.

Therefore, this reference frame permits to reset the information and the coordinates of the patient, of the points, but also of the acquisition and surgery tools, with respect to the pre-operative imaging.

In brief, the robotized arm provides a unique reference system permitting to identify and coordinate in the space, in real time, the various above-mentioned elements. Indeed, the <<modeled chain>> formed by the immobility of the patient's body with respect to the base of the robotized arm, as well as the arm itself until the end of the tool it carries, is sufficient per se to ensure an identification of each of the elements it is comprised of within a reference frame in the space. In order to achieve such a result, it is necessary to initialize such a chain, namely by identifying the elements it is comprised of. Such an initialization operation can be performed prior to the acquisition and during the latter, but also subsequently and during the intervention, through steps of updating of said chain. These updating operations occur automatically depending on the positioning of the tools and elements used, integral with said robotized arm.

Therefore, a repeatable nature intervenes in the positioning and displacement of the tools and elements, while this reproducible aspect could not be contemplated during the fully manual work of a practitioner, making them operator-dependent.

Furthermore, it is also possible to make the patient's body independent from the robotized arm and from its base. Therefore, an acquisition of the position of said patient should be performed in real time, in order to know exactly the changes in same, in order to get adapted to them.

Finally, the end of the robotized arm can also simultaneously carry means necessary for the acquisition and tools for the intervention. Indeed, it is then possible to contemplate, through miniaturized elements and tools, to integrate localization technologies, such as a laser, ultrasounds, a camera, mechanical tools or elements of surface or percutaneous telemetry coupled to tools, namely surgical tools. It is then possible to know in real time the positioning and the displacement of any of these elements, permitting an automation of the movements and paths of each of them, combined with acquisitions and three-dimensional surface resetting operations.

According to one embodiment, said identification means can be designed contactless, namely in the form of a radiation transmitter, for example a light transmitter, such as a laser beam, coupled to a distance sensor. In particular, said identification means can be in the form of a laser telemeter.

Other transmitters can be contemplated, using optical beams, acoustic waves, such as the ultrasounds or radio waves.

Thus, such identification means, located at the movable end of said robotized arm, can move around the anatomical surfaces to be scanned.

In this respect, an essential feature of the invention resides in that the scanning is divided into two successive steps.

A first step of the scanning consists of performing a preliminary identification of the coordinates of noteworthy points of said anatomical surfaces by manual displacement, assisted by said robotized arm, of said identification means at the level of said noteworthy points. This preliminary identification permits to determine a zone for scanning said anatomical surfaces.

In brief, the practitioner himself controls the displacement of the identification means, still integral with said robotized arm, in order to position them and to measure the coordinates of the specific points of the anatomical surfaces.

This step is operator-dependent, but sufficiently simple to be implemented in order to ensure a satisfactory reproducibility and accuracy of the coordinates of said noteworthy points.

The second step consists in performing an automatic scanning of the zone determined by said noteworthy points, by means of the robotized arm alone.

Thus, the manual identification permits to improve the automatic scanning by marking and delimiting the zone within which the coordinates will be measured, increasing the accuracy, limiting the risks of extrapolation and providing a capability of adapting the invention to the various morphologies of the anatomical surfaces.

According to a particular embodiment, said manual identification records the coordinates of at least three noteworthy points among 4, 5, 6 or 7 in order to construct a reference frame. A fourth point can be determined by symmetry with respect to three other points already targeted. In particular, in the case of a face, said fourth point can be obtained from one of said three noteworthy points by symmetry with respect to an axis passing through the other two of said noteworthy points. Further noteworthy intermediate points can be identified manually by the practitioner, depending on the cases and the morphology of the anatomical surfaces involved.

Then, a reference frame for calculating the path of the automatic scanning is determined, said reference frame being formed by at least two axes A-A' and B-B', each comprising a pair 4,5 and 6,7 of said four noteworthy points.

Figure 2:
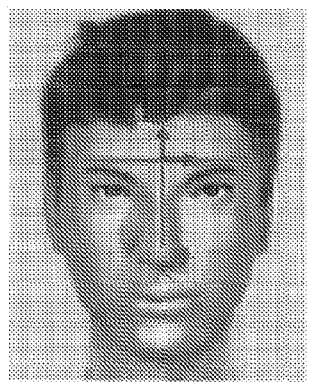
Figure 3:
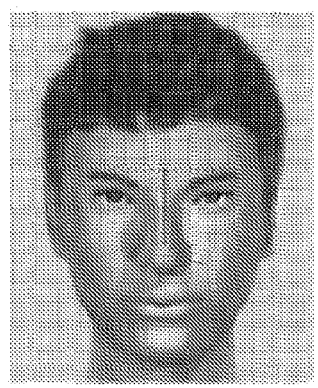

In the exemplary implementation shown in FIGS. 1 to 3, said anatomical surfaces correspond to the face 1. In addition, said axes A-A' and B-B' follow at least partially the nose rim and a frontal line, respectively, the nose rim being substantially vertical, while the frontal line is substantially horizontal. Said noteworthy points can then correspond: for point 4 to the center of the forehead, for point 5 to the end of the nose bone, and for point 6 to a point of the left end of the forehead, while point 7 corresponds to the opposite end.

It should be noted that the points 4 and 5 determine the height of the zone to be scanned, while the points 6 and 7, located on each side of the face 1, permit to determine the width of said zone.

In addition, the invention foresees to perform a first bringing into correspondence with the help of said thus defined frame.

To this end, the invention consists in performing an identification of the coordinates of at least one central point 8. In particular, said central point 8 is located at the intersection of said axes A-A' and B-B'.

Said central point 8 will serve as a center, in order to perform this preliminary surface resetting.

To reach this, said central point 8 should be recorded at the level of the first model 2, i.e. on the imaging performed before the operation.

Then, a three-dimensional intermediate representation in the form of a digital intermediate model is created. In brief, this intermediate model can include any of the noteworthy points 4 to 7, as well as the central point 0 and/or the axes A-A' and B-B'.

Afterwards, a bringing into correspondence is performed through a preliminary resetting of said first model 2 with said intermediate model, by bringing into correspondence said central point 8 and at least another noteworthy point 4 to 7. This intermediate bringing into correspondence can also be performed by means of said so defined reference frame, by correspondence of said axes A-A' and B-B'.

This pre-resetting thus permits to more efficiently adjust the models 1 and 2 during the final resetting.

Said preliminary resetting (and the associated data-processing calculation time) can also intervene during the automatic scanning step.

In this respect, once the scanning zone has been determined, the scanning path is calculated in order to optimize the number and the distribution of the points identified within said zone.

Figure 4:
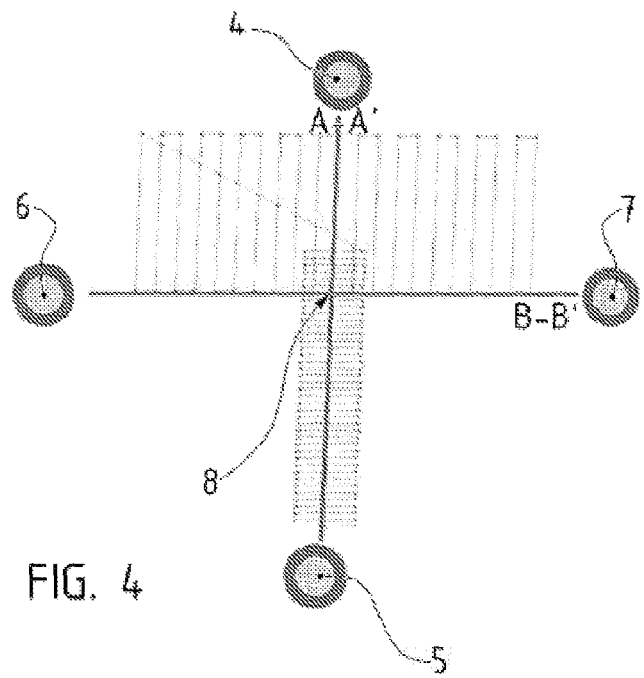
FIG. 4 schematically represents a detailed schematic view of the possibility of the automatic scanning step according to the invention.

A non-restrictive exemplary path is schematically shown in FIG. 4. One observes that the path follows the axis B-B' from the point 6 towards the point 7, in the upper portion of the reference frame, then follows symmetrically the axis A-A' from top to bottom, from the underside of the point 4 to the point 5.

It should be noted that in the example the displacement occurs in the form of a toothed and continuous path. However, any kind of displacement can be contemplated, according to various continuous or discontinuous curves adapted depending on the morphology of the anatomic zone involved.

Furthermore, all the digital data in the meaning of the present invention (models, coordinates or algorithm) and their implementation (recording, modification or display) are processed through adapted data-processing means. The same apply to the programming and the digital controls of said robotized arm.

The method for contactless acquisition according to the invention provides a reliable and reproducible and methodology, quick and easy to be implemented by any practitioner, for an accurate result, avoiding errors related to the operator, while preserving an improvement thanks to the adaptability depending on the practitioner and his medical experience. In particular, the operator can correct the initial path, providing an intelligent and cooperative aspect, but also flexibility with the advantages provided by the strictness and precision of the robotic automatism.

Of course, the invention is not limited to the examples shown and described above, which can have variants and modifications without therefore departing from the framework of the invention.

We claim:

1. Method for automated and assisted acquisition of anatomical surfaces, said method comprising the steps of:
   creating a first three-dimensional representation in a form of a first digital model by a first acquisition of anatomical surfaces;
   creating a second three-dimensional representation in a form of a second digital model by a second perioperative acquisition by scanning said surfaces, wherein a means for identifying coordinates of said surfaces performs said scanning, said means for identifying being supported by a robotized arm;
   resetting said first digital model and said second digital model for bringing into correspondence;
   wherein said scanning comprises:
      performing a preliminary identification of coordinates of noteworthy points of said anatomical surfaces by manual displacement, assisted by said robotized arm, and identification of said means for identifying at a level of said noteworthy points, so as to construct a reference frame and to determine a scanning zone for said anatomical surfaces;
      creating an intermediate model from said reference frame and at least one of said noteworthy points;
      performing a preliminary resetting of said first digital model with said second digital model;
   performing an automatic scanning of said scanning zone;
   performing an identification of coordinates of at least three noteworthy points;

determining a fourth noteworthy point from one of said three noteworthy points by symmetry according to an axis passing through the other two of said noteworthy points; and determining said reference frame for calculating a path of said automatic scanning, said reference frame being formed of at least two axes, each axes comprising a pair of said four noteworthy points.

2. Acquisition method according to claim 1, further comprising the step of:

performing an identification of the coordinates of at least a central point, said central point being located at the intersection of said axes.

3. Acquisition method according to claim 2, further comprising the step of:

recording said central point at a level of the first model, wherein said preliminary resetting is performed through bringing into correspondence of said central point and at least another noteworthy point.

4. Acquisition method according to claim 3, further comprising the step of:

performing bringing into correspondence of said first digital model with said intermediary model, by correspondence of said axes.

5. Acquisition method according to claim 2, wherein said anatomical surfaces correspond to a face and said axes follow at least partially a nose rim and a frontal line.

6. Acquisition method according to claim 1, further comprising the step of: determining a reference frame centered on said robotized arm.

7. A method for automated and assisted acquisition of anatomical surfaces during a preparation and carrying out of a surgical intervention, said method comprising:

acquiring an initial digital model before surgical intervention;

performing an identification of coordinates of at least three noteworthy points of anatomical surfaces, in a manual acquisition step, by handling a robotized arm supporting identifying means;

determining a fourth noteworthy point from one of said at least three noteworthy points by symmetry according to an axis passing through the other two of said noteworthy points;

determining a reference frame for calculating a path of an automatic scan, said reference frame being formed of at least two axes, each axis comprising a pair of said four noteworthy points;

creating an intermediate digital model from said reference frame and at least one of said noteworthy points;

performing said automatic scan along said path of said automatic scan with said robotized arm in an automatic scanning step, said identifying means creating a preoperative digital model;

resetting said initial digital model with said intermediate digital model in a preliminary resetting process step so as to bring said initial digital model and said intermediate digital model into correspondence; and forming a final digital model by resetting said initial digital model with said preoperative digital model in a final resetting process step, said final digital model being based on said initial digital model being already reset in said preliminary resetting process step with said preoperative model.

8. The method according to claim 7, wherein said manual acquisition step further comprises: pointing out coordinates of at least a central point located at an intersection of said axes of said reference frame.

9. The method according to claim 8, wherein said central point is recorded at a level of said initial digital model, said preliminary resetting process step being comprised of bringing into correspondence said central point with at least another noteworthy point.

10. The method according to claim 9, wherein said preliminary resetting process step further comprises: bringing into correspondence said initial digital model with said intermediary digital model, by correspondence of said axes.

11. The method according to claim 8, wherein said anatomical surfaces correspond to a face, and wherein said axes follow at least partially a nose rim and a frontal line.

12. The method according to claim 7, wherein said reference frame is centered on said robotized arm.

* * * * *